(12) United States Patent
Kockler

(10) Patent No.: US 10,106,476 B1
(45) Date of Patent: *Oct. 23, 2018

(54) ENERGY EFFICIENT METHODS FOR ISOMERIZATION OF A C5-C7 FRACTION WITH DIVIDING WALL FRACTIONAL DISTILLATION

(71) Applicant: David Norbert Kockler, Arlington Heights, IL (US)

(72) Inventor: David Norbert Kockler, Arlington Heights, IL (US)

(*) Notice: Subject to any disclaimer, the term of this patent is extended or adjusted under 35 U.S.C. 154(b) by 0 days.

This patent is subject to a terminal disclaimer.

(21) Appl. No.: 15/703,382

(22) Filed: Sep. 13, 2017

Related U.S. Application Data

(63) Continuation-in-part of application No. 15/476,774, filed on Mar. 31, 2017.

(51) Int. Cl.
*C07C 5/27* (2006.01)
*C07C 7/04* (2006.01)
*B01D 3/14* (2006.01)

(52) U.S. Cl.
CPC ............ *C07C 5/2732* (2013.01); *B01D 3/141* (2013.01); *B01D 3/143* (2013.01)

(58) Field of Classification Search
None
See application file for complete search history.

(56) References Cited

U.S. PATENT DOCUMENTS

| | | | | |
|---|---|---|---|---|
| 6,395,950 B1* | 5/2002 | Rice | ....................... | B01D 3/141 585/734 |
| 6,540,907 B1* | 4/2003 | Towler | ................... | B01D 3/141 208/211 |
| 6,552,242 B1* | 4/2003 | Rice | ....................... | B01D 3/141 208/347 |
| 6,927,314 B1* | 8/2005 | Schultz | .................. | B01D 3/141 585/734 |
| 7,429,685 B2* | 9/2008 | Bouchy | .................. | C10G 65/14 585/301 |
| 2016/0311732 A1* | 10/2016 | Banerjee | ................ | C10G 65/08 |

* cited by examiner

*Primary Examiner* — Philip Y Louie

(57) ABSTRACT

This invention relates to a method of separating an isomerization zone effluent mixture comprising between 5 and 8 carbon atoms into high octane isomerate product streams and low octane streams which may be recycled to the isomerization zone. The separation process makes use of a dividing wall column to efficiently perform the separation of high octane multibranched paraffins from low octane straight chain and single branched paraffins.

17 Claims, 5 Drawing Sheets

ENERGY EFFICIENT METHODS FOR ISOMERIZATION OF A C5-C7 FRACTION WITH DIVIDING WALL FRACTIONAL DISTILLATION

CROSS REFERENCE

The present application is a Continuation In Part of U.S. application Ser. No. 15/476,774 filed on Mar. 31, 2017.

BACKGROUND OF THE INVENTION

This invention relates generally to the isomerization of hydrocarbons. More specifically, the invention involves an isomerization zone and an isomerized product fractionation zone in which a stabilized effluent stream from the isomerization zone is separated into high octane product streams and low octane product streams by means of fractional distillation and by making use of a dividing wall column and a non-divided column. The stabilized isomerization zone effluent is generally comprised of hydrocarbons containing between 5 and 8 carbon atoms per molecule.

Isomerization is an important process used in the petroleum industry to increase the research octane number (RON) of light naphtha feeds. In current practice, the naphtha (C5-C10 fraction) obtained from atmospheric distillation of petroleum is separated by means of fractional distillation into light naphtha (C5-C6 fraction or C5-C7 fraction depending on desired volume of light naphtha) and heavy naphtha (C7-C10 fraction or C8-C10 fraction depending on desired volume of light naphtha). The light naphtha is generally sent to an isomerization process unit and the heavy naphtha is generally sent to a catalytic reforming process unit. In both the isomerization process unit and the catalytic reforming process unit, the RON values of the respective naphtha fractions are improved. High RON values are a desired characteristic for naphtha streams that are sent to the gasoline pool because gasoline spark ignition engines perform better and can achieve greater fuel efficiency with higher RON gasoline.

The product streams from isomerization processes (isomerate), unlike the product streams from catalytic reforming processes (reformate) are virtually free of aromatic compounds. Low aromatic concentrations are a desired characteristic for naphtha streams that are sent to the gasoline pool because of increasingly stringent specifications for aromatics in gasoline. As a result of the increasingly stringent specifications for aromatics in gasoline, there has been growing interest in the petroleum industry in processing a greater volume of light naphtha in isomerization process units.

The present invention relates in particular to C5-C7 fraction light naphtha feeds to isomerization units that are rich in C5-C8 molecules. The C5-C7 fraction is generally produced through fractionation of full range naphtha in such a manner that the majority of the C8 molecules found in the full range naphtha are excluded from the C5-C7 fraction. However, a small percentage of the C8 molecules from the full range naphtha will be included in the C5-C7 fraction as a result of overlap that is characteristic of distillation processes. Therefore, the term "C5-C7 fraction" will be used herein to designate a fraction that contains C5-C8 molecules but in practice is materially a C5-C7 fraction.

Several processes for isomerizing C5-C7 fraction light naphtha feeds are described in the patent literature. Two such examples of recent patents are U.S. Pat. No. 6,338,791 and U.S. Pat. No. 7,429,685. U.S. Pat. No. 6,338,791 describes various process flow schemes to isomerize a C5-C7 fraction and separate the isomerization reactor effluent into high octane streams and low octane streams. U.S. Pat. No. 7,429,685 describes various process flow schemes in which the C5-C7 fraction is first separated into a C5-C6 fraction and a C7 fraction before passing the two fractions independently to two parallel isomerization reactors, from where the isomerization reactor effluents are separated into high octane streams and low octane streams. U.S. Pat. No. 7,429,685 describes several separation configurations; in one configuration the reactor effluents are separated independently, and in another configuration the reactor effluents are combined and separated.

The separation of the isomerate reactor effluent in isomerization processes is critical to achieving the desired RON target for the isomerate product. In order to maximize the isomerate product RON, it is desirable to separate the isomerization reactor effluent into different molecular structural classes. In general, multibranched paraffins (paraffins having two or more branches) have higher RON values than straight chain and single branched compounds. It is desirable, therefore, to separate the high octane multibranched compounds (as well as high octane isopentane) as isomerate product and recycle lower octane straight chain and single branched paraffins to the reactor feed. It is generally not desirable to recycle multibranched paraffins to the reactor feed because doing so would result in the conversion of a portion of the high octane multibranched paraffins into lower octane straight chain and single branched paraffins in the isomerization reactor.

Several methods that have been utilized to achieve the desired separation between high octane components and low octane components in isomerization reactor effluents in applications with C5-C6 fraction light naphtha feeds are described in Domergue, B., and Watripont, L. *World Refining, May* 2000, p. 26-30.

None of the methods outlined in the Domergue and Watripont article make use of a dividing wall column to separate high octane components and low octane components in isomerization reactor effluents. In general, a significant improvement in the efficiency of separation can be achieved through separations that are performed in dividing wall columns compared with the use of multiple non-divided columns to perform the same separations because of the superior thermal efficiency of dividing wall columns. An alternate scheme for achieving the desired separation between high octane components and low octane components in isomerization reactor effluents in applications with C5-C6 fraction light naphtha feeds using a combination of adsorption and a dividing wall column is described in U.S. Pat. No. 6,395,951.

Separating isomerization reactor effluents in applications with C5-C7 fraction light naphtha feeds is significantly more complicated than in applications with C5-C6 fraction light naphtha feeds, especially when high values of isomerate RON are required. Schemes that require the use of a deisohexanizer to recover and recycle methylpentane compounds (single branch C6 paraffins) in applications with C5-C6 fraction light naphtha feeds increase in complexity in applications with C5-C7 fraction light naphtha feeds and require the use of a deisohexanizer and a deisoheptanizer to achieve a high isomerate product RON. Deisohexanizer columns are generally large, costly to construct and install, and consume large amounts of reboiler energy because of the difficult separation between close boiling high octane multibranched C6 paraffins such as dimethylbutanes and low octane single branched C6 paraffins such as methylpentanes.

Deisoheptanizer columns present the same drawbacks as deisohexanizer columns because of the difficult separation between close boiling high octane multibranched C7 paraffins such as dimethylpentanes and low octane single branched C7 paraffins such as methylhexanes.

An example of a conventional method for separating a combined isomerization zone effluent mixture by fractionation into high octane and low octane streams is shown in FIG. 1. The charge to the isomerization process is sent via line 12 to charge fractionation zone 20. The charge fractionation zone may produce one or more primary feeds to the isomerization zone. Two primary feeds to the isomerization zone are shown in the example in FIG. 1. The two primary feeds are conducted from the charge fractionation zone 20 to isomerization zone 22 via lines 14 and 16. In the example shown in FIG. 1, the stream that is conducted via line 14 represents a C5-C6 fraction and the stream that is conducted via line 16 represents a C7 fraction. Two recycle streams from the isomerized product fractionation zone are also sent to the isomerization zone. A C6 rich recycle stream is conducted via line 42 and mixed with the C5-C6 fraction primary feed to create a combined C5-C6 isomerization zone feed stream which is conducted via line 18 to isomerization zone 22. A C7 rich recycle stream is conducted via line 34 and mixed with the C7 fraction primary feed to create a combined C7 isomerization zone feed stream which is conducted via line 24 to isomerization zone 22. Two reactor effluent streams exit the isomerization zone via lines 26 and 28 and are sent to two independent stabilizers (not shown in FIG. 1) to remove butane and lighter hydrocarbons. A stabilized isomerized product is removed from each of the two stabilizers.

The stabilized isomerized product corresponding to a C5-C6 fraction is sent via line 26 to deisohexanizer column 38. The C5-C6 fraction isomerized product is separated into three streams in the deisohexanizer column: a first high octane stream comprising the major portion of hydrocarbons containing 5 carbon atoms and paraffins containing 6 carbon atoms with at least two branches is removed from the first end of the column via line 40, a low octane stream comprising the major portion of normal hexane and paraffins containing 6 carbon atoms and a single branch is removed as a side stream from an intermediate point in the column via line 42, and a second high octane stream comprising the major portion of hydrocarbons containing at least 7 carbon atoms is removed from the second end of the column via line 44 (note that this stream may optionally be recycled to the isomerization zone or to the charge fractionation zone). The term "first end of the column" is used herein to refer to the overhead distillate system (at the top) of the column and the term "second end of the column" is used herein to refer to the bottom of the column.

The stabilized isomerized product corresponding to a C7 fraction is sent via line 28 to deisoheptanizer column 30. The C7 fraction isomerized product is separated into three streams in the deisoheptanizer column: a first high octane stream comprising major portion of hydrocarbons containing 6 carbon atoms and paraffins containing 7 carbon atoms with at least two branches is removed from the first end of the column via line 32, a low octane stream comprising the major portion of normal heptane and paraffins containing 7 carbon atoms and a single branch is removed as a side stream from an intermediate point in the column via line 34 and a second high octane stream comprising the major portion of hydrocarbons containing at least 8 carbon atoms is removed from the second end of the column via line 36.

A conventional method for separating isomerization zone effluent streams as shown in FIG. 1 is energy inefficient because high energy inputs are required for each of the two columns to achieve the required separation of high octane and low octane streams. High energy inputs are required for both columns because each of the two columns are designed to separate close boiling high octane multibranched paraffins and low octane single branched paraffins.

The separation scheme presented in U.S. Pat. No. 6,395,951 employs a unique configuration consisting of an adsorptive separation zone followed by a dividing wall fractionation zone to separate isomerization zone effluent streams into high octane and low octane fractions. Low octane straight chain paraffins such as normal hexane are removed in the absorptive separation zone for recycle to the isomerization zone and a dividing wall column in the dividing wall fractionation zone separates low octane single branched C6 paraffins from high octane multibranched C6 paraffins and from a high octane C6-C7 bottoms stream. The separation in the dividing wall column for this design is notably different than separations which are made in typical deisohexanizer column designs in that the majority of (high octane) methylcyclopentane is intentionally removed as part of the high octane C6-C7 bottoms stream. This contrasts with a typical deisohexanizer design that does not have an adsorptive separation section to remove low octane straight chain paraffins. Normal hexane (a straight chain molecule) is present in the feed to a typical deisohexanizer design that does not have an adsorptive separation section to remove low octane straight chain paraffins, and because normal hexane has a very low octane value, it is desirable to include as much normal hexane as possible in the low octane fraction containing low octane paraffins with a single branch so that the normal hexane can be recycled to the isomerization zone for conversion to isomerized products. Normal hexane and methylcyclohexane are close boiling molecules, and as a result of including the majority of normal hexane in the low octane fraction containing low octane C6 paraffins with a single branch, the majority of methylcyclopentane is also removed from a typical deisohexanizer column in the low octane stream containing normal hexane and C6 paraffins with a single branch. In effect, the methods described in U.S. Pat. No. 6,395,951 use a dividing wall column to create high octane and low octane fractions that have different compositions with respect to methylcyclopentane than typical deisohexanizer separations.

The unique manner in which the method outlined in U.S. Pat. No. 6,395,951 using absorptive separation in conjunction with fractional distillation means that in order to apply this method to separate isomerization zone effluent streams in applications with C5-C7 fraction light naphtha feeds, at least two dividing wall columns would be required; one to segregate low octane single branched C6 paraffins for recycle to the isomerization zone and a second to segregate low octane single branched C7 paraffins for recycle to the isomerization zone. Each of the two dividing wall columns would require high energy input to achieve the desired separation between close boiling low octane single branched paraffins and high octane multibranched paraffins, which makes the approach described in U.S. Pat. No. 6,395,951 poorly suited for applications with C5-C7 fraction light naphtha feeds.

The use of a fractional distillation scheme involving a dividing wall column and a non-divided column in the present invention to separate a combined isomerization reactor effluent in a process with a C5-C7 fraction light naphtha feed provides significant advantages versus methods that are currently publically known because the energy intensive separations between close boiling high octane multibranched paraffins and low octane single branched paraffins are combined into a single dividing wall column, thereby reducing the amount of distillation energy input associated with conventional fractionation techniques.

BRIEF SUMMARY OF THE INVENTION

One purpose of the invention is to separate a combined reactor effluent from one or more isomerization reactors into high octane streams and low octane streams for the purpose of producing a high octane isomerate product and recycling the low octane streams to one or more isomerization reactors. The combined isomerization reactor effluent stream is generally passed to a stabilizer column which provides a stabilized isomerized product stream that is removed from the bottom of the stabilizer column. The process which is used to perform the separation of the stabilized isomerized product may create one or more intermediate streams. The term "intermediate stream" is used herein to describe a stream that has not yet been fully separated into high octane and low octane fractions and requires further separation to divide the stream into high octane and low octane fractions. The invention will separate the stabilized isomerized product stream comprising C5-C8 paraffins with varying degrees of branching into high octane Fraction A comprising the major portion of hydrocarbons containing 5 carbon atoms and paraffins containing 6 carbon atoms with at least two branches, low octane Fraction B comprising the major portion of normal hexane and paraffins containing 6 carbon atoms and a single branch, high octane Fraction C comprising the major portion of paraffins containing 7 carbon atoms with at least two branches, low octane Fraction D comprising the major portion of normal heptane and paraffins containing 7 carbon atoms and a single branch, and high octane Fraction E comprising the major portion of hydrocarbons containing at least 8 carbon atoms. The term "major portion of" is used herein to refer to the major portion of referenced molecules which are present in all of the feed streams that are sent to the dividing wall column in the isomerized product fractionation zone. For example, if a single column feed consisting of a stabilized isomerized product stream is fed to the dividing wall column in the isomerized product fractionation zone contains 99 hydrocarbon molecules with at least 8 carbon atoms, then Fraction E will contain at least 50 hydrocarbon molecules with at least 8 carbon atoms.

The stabilized isomerized product mixture is separated in a process that includes a dividing wall column and a non-divided column. The mixture is introduced into a dividing wall column which is divided into first and second parallel fractionation zones by a dividing wall that extends from a lower end to an upper end within the column, with the first and second parallel fractionation zones being in open communication at the upper ends of each fractionation zone with an upper section of the column that is undivided and with the first and second parallel fractionation zones being in open communication at the lower ends of each fractionation zone with a lower section of the column that is undivided. The first parallel fractionation zone is defined as the parallel fractionation zone on the feed side of the dividing wall (the parallel fractionation zone on the side of the dividing wall which faces the stabilized isomerized product feed entry point into the column) and the second parallel fractionation zone is defined as the parallel fractionation zone on the side of the dividing wall which faces away from the first parallel fractionation zone.

The stabilized isomerized product mixture is introduced to the dividing wall column at an intermediate point of the first fractionation zone. An intermediate stream comprising the major portion of normal hexane and paraffins containing 6 carbon atoms and a single branch and the major portion of hydrocarbons containing 7 carbon atoms with at least two branches is removed from an intermediate point of the second fractionation zone of the dividing wall column. The intermediate stream comprising the major portion of normal hexane and paraffins containing 6 carbon atoms and a single branch and the major portion of hydrocarbons containing 7 carbon atoms with at least two branches is passed to a non-divided second column. A high octane stream comprising the major portion of hydrocarbons containing 5 carbon atoms and paraffins containing 6 carbon atoms with at least two branches is removed from the first end of the dividing wall column and a second high octane stream comprising the major portion of hydrocarbons containing at least 8 carbon atoms is removed from the second end of the dividing wall column. A low octane stream comprising the major portion of normal heptane and paraffins containing 7 carbon atoms and a single branch is removed as a side stream from an intermediate point in the lower undivided section of the dividing wall column. A low octane stream comprising the major portion of normal hexane and paraffins containing 6 carbon atoms and a single branch is removed from the first end of the non-divided column and a high octane stream comprising the major portion of hydrocarbons containing 7 carbon atoms with at least two branches is removed from the second end of the non-divided column.

DETAILED DESCRIPTION OF THE INVENTION

The detailed description is provided herein is exemplary and provides examples of preferred embodiments of the invention. The description of the exemplary embodiments is not intended to limit the use of the invention to only the exemplary embodiments of the invention described herein.

The invention is not restricted to any particular type of isomerization process; however, the invention is particularly well suited for isomerization processes which process a light naphtha charge comprised of a C5-C7 fraction. The invention is also particularly well suited for applications in which recycle of low octane isomerized products is required to meet the RON specification for the isomerate product from the overall isomerization process.

The overall isomerization process for processing a C5-C7 light naphtha charge can be generally described as divided into three zones: a charge fractionation zone, where the charge is separated into two or more fractions which may be processed independently in the downstream isomerization zone; an isomerization zone; and an isomerized product fractionation zone where the combined reactor effluent is stabilized and the stabilizer bottoms is separated into high octane isomerate product streams and low octane recycle streams. The term "overall isomerization process" is used herein to refer to the entirety of the isomerization process. The invention provides an improvement to the processes in the isomerized product fractionation zone.

The isomerization zone may be any form of isomerization zone which processes one or more feed streams containing C5-C7 straight chain hydrocarbons and branched chain hydrocarbons and converts the straight chain hydrocarbons into branched chain hydrocarbons and converts branched chain paraffins into paraffins with an increased degree of branching. Suitable feeds to the isomerization zone will contain at least one component from the following group: normal pentane, normal hexane, and normal heptane.

The isomerization zone may be comprised of one or more isomerization reactor systems as described in U.S. Pat. No. 7,429,685 (note that U.S. Pat. No. 7,429,685 makes reference to two parallel isomerization zones in contrast to the single isomerization zone with one or more reactor systems that is described herein). U.S. Pat. No. 7,429,685 describes a process in which the isomerization process charge is separated into at least two fractions (C5-C6 fraction and C7 fraction) for independent processing of the two fractions under different isomerization reactor conditions in order to optimize the RON value of the resulting isomerate products. Refer to U.S. Pat. No. 7,429,685 for additional information regarding suitable isomerization catalysts and preferred isomerization reaction conditions for different feed fractions.

Figure 1:
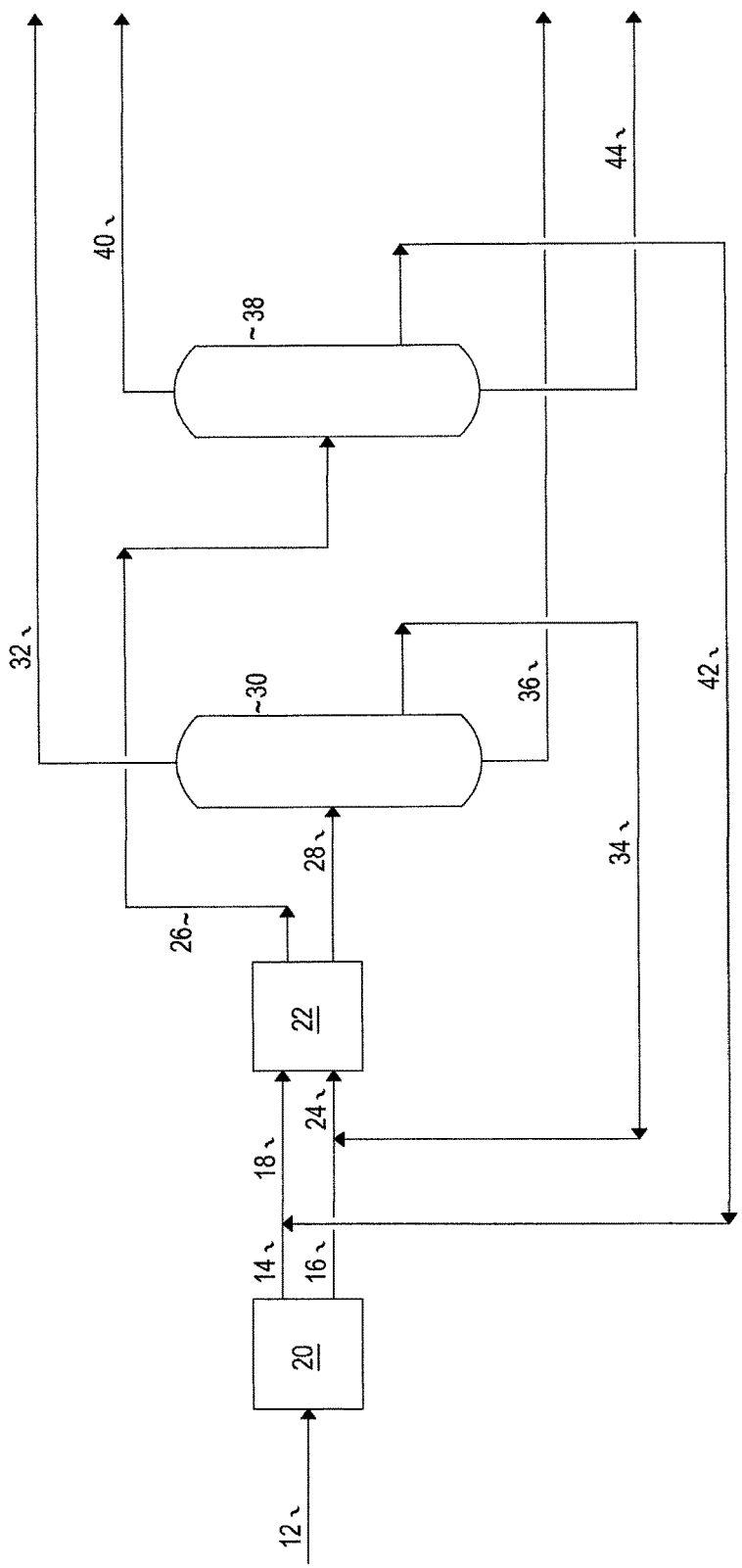
FIG. 1 provides a simplified process flow diagram that shows a conventional method of parallel fractionation of two isomerization zone effluent mixtures using two non-divided columns.
Figure 2:
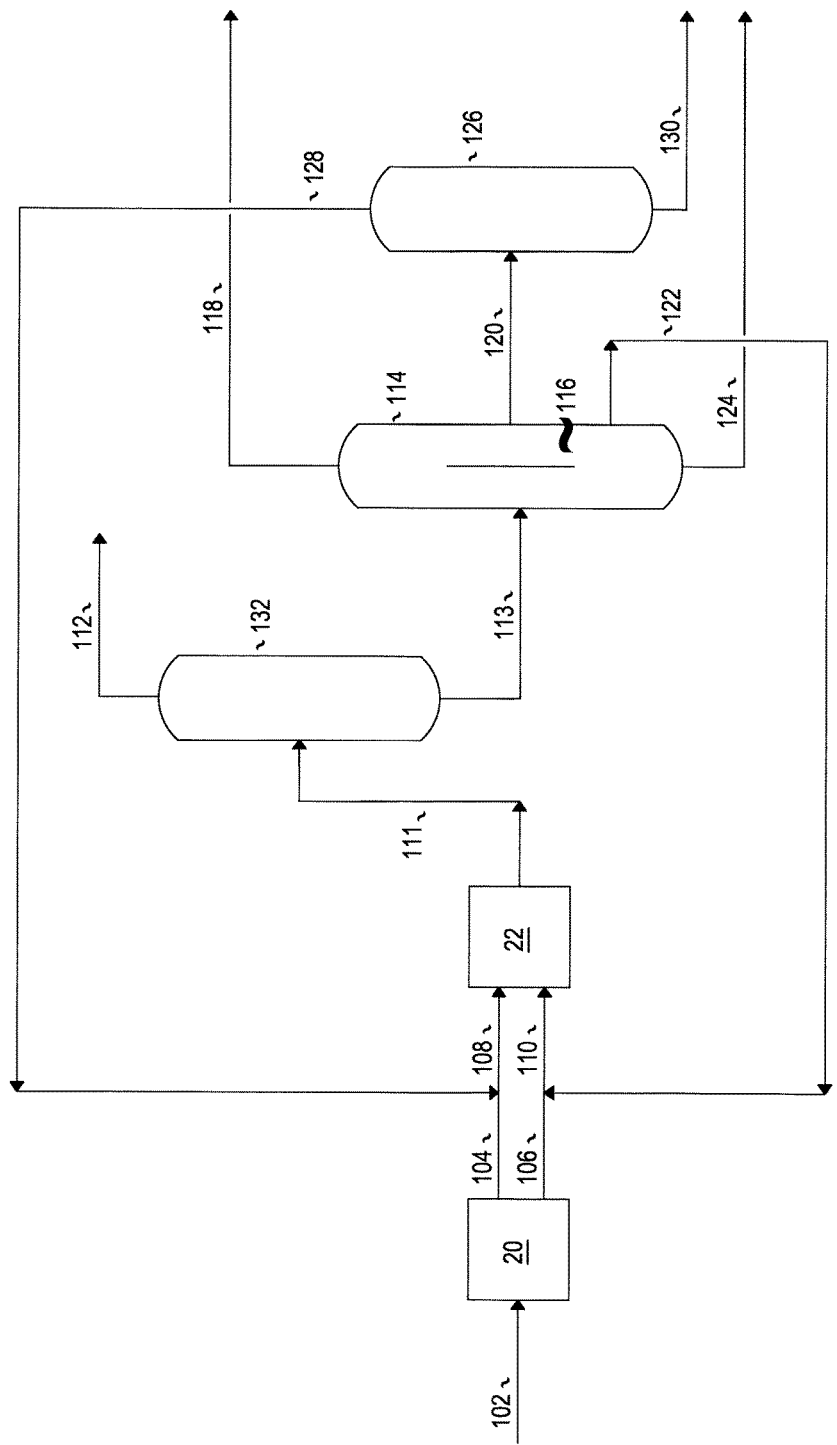
FIG. 2 provides a simplified process flow diagram of a first preferred embodiment of the invention.

A first exemplary embodiment of the invention is shown in FIG. 2. This drawing is a simplified process flow diagram which does not show details for the process system such as instrumentation and controls, valves, pumps, reboilers, condensers, and heat exchangers. Such details are known to experienced practitioners of the art.

The charge to the isomerization process is sent via line 102 to charge fractionation zone 20. The charge fractionation zone may produce one or more primary feeds to the isomerization zone. Two primary feeds to the isomerization zone are shown in FIG. 2. The two primary feeds are conducted from the charge fractionation zone 20 to isomerization zone 22 via lines 104 and 106. In this exemplary embodiment of the invention, the stream that is conducted via line 104 represents a C5-C6 fraction and the stream that is conducted via line 106 represents a C7 fraction. Two recycle streams from the isomerized product fractionation zone are also sent to the isomerization zone. A C6 rich recycle stream is conducted via line 128 and mixed with the C5-C6 fraction primary feed to create a combined C5-C6 isomerization zone feed stream which is conducted via line 108 to isomerization zone 22. A C7 rich recycle stream is conducted via line 122 and mixed with the C7 fraction primary feed to create a combined C7 isomerization zone feed stream which is conducted via line 110 to isomerization zone 22.

Isomerization zone 22 shown In FIG. 2 illustrates the isomerization equipment and processes used to efficiently isomerize the isomerization zone feeds which are conducted via lines 108 and 110 to the isomerization zone. Each of the isomerization zone feeds are isomerized in isomerization zone 22 in the presence of isomerization catalysts and hydrogen. Isomerization may take place in one or more isomerization reactor systems, wherein a reactor system may contain one or more isomerization reactors in series arrangement. Each isomerization reactor system may contain different isomerization catalysts and each reactor system may operate at different isomerization conditions in order to efficiently isomerize the isomerization zone feeds. In the exemplary embodiment of the invention shown in FIG. 2, the C5-C6 isomerization zone feed is intended to be isomerized in an isomerization reactor system designed for isomerizing C5-C6 feeds and the C7 isomerization zone feed is intended to be isomerized in an isomerization reactor system designed for isomerizing C7 feeds. The reactor effluent streams from all of the reactor systems are combined into a single combined isomerization zone effluent in the exemplary embodiment shown in FIG. 2. In the present invention, however, more than one isomerization zone effluent may be sent from the isomerization zone to the isomerized product fractionation zone.

The combined effluent stream from the isomerization reactors which is removed from isomerization zone 22 is sent to stabilizer 132 via line 111 to remove butane and light gases. A stabilized isomerized product is removed from the second end of stabilizer 132 and sent to a fractionation system consisting of a dividing wall column and a non-divided column to separate high octane streams from low octane streams. Butane and light gases are removed from the first end of stabilizer 132 via line 112. The stabilized isomerized product is sent to dividing wall column 114 via line 113. The dividing wall column contains two parallel fractionation zones which are divided by a vertical dividing wall 116. The dividing wall is imperforate and therefore prevents flow of vapor or liquid from one parallel fractionation zone across the dividing wall to the other parallel fractionation zone. Above the top of each of the two parallel fractionation zones is an upper undivided fractionation zone and below the bottom of each of the two parallel fractionation zones is an lower undivided fractionation zone. Each of the two parallel fractionation zones are in open communication at the top of the parallel fractionation zones with the upper undivided fractionation zone and each of the two parallel fractionation zones are in open communication at the bottom of the parallel fractionation zones with the lower undivided fractionation zone. This arrangement restricts the flow of vapor and liquid from crossing from one parallel fractionation zone to another through the dividing wall but allows vapor and liquid to flow around the dividing wall from one parallel fractionation zone to another.

To simplify the discussion of the separation which takes place in dividing wall column 114, the separation will be discussed in terms of the following five fractions which are produced from the isomerized product fractionation zone: Fraction A comprising the major portion of hydrocarbons containing 5 carbon atoms and paraffins containing 6 carbon atoms with at least two branches, which represents the fraction with the lowest boiling point, Fraction B comprising the major portion of normal hexane and paraffins containing 6 carbon atoms and a single branch, which represents the fraction with the second lowest boiling point, Fraction C comprising the major portion of paraffins containing 7 carbon atoms with at least two branches, which represents the fraction with the third lowest boiling point, Fraction D comprising the major portion of normal heptane and paraffins containing 7 carbon atoms and a single branch, which represents the fraction with the fourth lowest boiling point, and Fraction E comprising the major portion of hydrocarbons containing at least 8 carbon atoms which represents the fraction with the highest boiling point.

Fractions A, C, and E are rich in high octane components which makes it advantageous to use these fractions as constituents of the isomerate product that is produced in the overall isomerization process. Fractions B and D are rich in low octane components which can be further isomerized to produce high octane components. Therefore it would be more advantageous to recycle Fractions B and D to the isomerization zone rather than to use these fractions as constituents of the isomerate product that is produced in the overall isomerization process. Recycling Fractions B and D to the isomerization zone increases the octane of the composite isomerate product from the overall isomerization process.

The stabilized isomerized product is introduced at an intermediate point to the feed side, or first parallel fractionation zone, of the dividing wall column. The entirety of Fraction A as well as a portion of Fractions B and C are driven upwards in the first parallel fractionation zone and enter the upper undivided section of the column. In the upper undivided section of the column, Fraction A is driven upwards to the top of the column and the portions of Fractions B and C which were driven upwards in the first parallel fractionation zone drain down into the second parallel fractionation zone. Fraction A is removed via line 118 from the first end of the column as a high octane isomerate product stream.

The entirety of Fractions D and E as well as a portion of Fractions B and C drain down through the first parallel fractionation zone and enter the lower undivided section of the column. The portions of Fractions B and C which drained down through the first parallel fractionation zone are driven upward into the second parallel fractionation zone.

Within the second parallel fractionation zone, the portions of Fractions B and C which were driven upwards in the first parallel fractionation zone and drained down into the second parallel fractionation zone combine with the portions of Fractions B and C which drained down through the first parallel fractionation zone and were driven upward into the second parallel fractionation zone. The entirety of Fractions B and C are removed from an intermediate point in the second parallel fractionation zone via line 120 as a first side draw from the column.

In the lower undivided section of the column, Fraction E drains down to the bottom of the column and Fraction D drains down to an intermediate point in the lower undivided section of the column. Fraction E is removed via line 124 from the second end of the column as a high octane isomerate product stream. Fraction D is removed via line 122 from an intermediate point in the lower undivided section of the column as a second side draw from the column and returned to the isomerization zone.

The mixture containing Fractions B and C that is removed from an intermediate point of the second parallel fractionation zone of the column is sent via line 120 to an intermediate point in non-divided column 126, where Fraction B is separated from Fraction C. Fraction B is removed from the first end of the column and returned via line 128 to the isomerization zone. Fraction C is removed from the second end of the column via line 130 as a high octane isomerate product stream.

The composite high octane isomerate product from the overall isomerization process in the first exemplary embodiment is comprised from the sum of Fractions A, C, and E. Each of these three fractions are removed from the isomerized product fractionation zone and combined to form the composite isomerate product from the overall isomerization process.

In the first exemplary embodiment of the invention shown in FIG. 2, four streams are removed from the dividing wall column. In this embodiment, Fractions D and E are separated in the lower undivided section of the dividing wall column. It is also possible, however, to perform the separation of Fractions D and E in a second non-divided column by removing only three streams rather than four from the dividing wall column. In a scenario where Fractions D and E are separated in a second non-divided column, the entirety of Fractions D and E drain down to the bottom of the dividing wall column. The stream removed from the second end of the dividing wall column containing a mixture of Fractions D and E would be sent to a second non-divided column to separate Fractions D and E.

A second embodiment of the invention may be used in certain applications where a significant improvement can be made to the composite isomerate product RON by recycling C5 molecules in a C5 rich stream that is produced in the isomerized product fractionation zone back to the charge fractionation zone. In the charge fractionation zone, the C5 rich stream is separated into a high octane isopentane stream which is removed from the process as an isomerate product stream, and a low octane normal pentane stream which is sent to the isomerization zone together with the isomerization process charge. The use of a deisopentanizer in a charge fractionation zone to separate isopentane from a feed comprised of the isomerization process charge combined with a C5 recycle stream from the isomerized product fractionation section is well known to experienced practitioners of the art.

Figure 3:
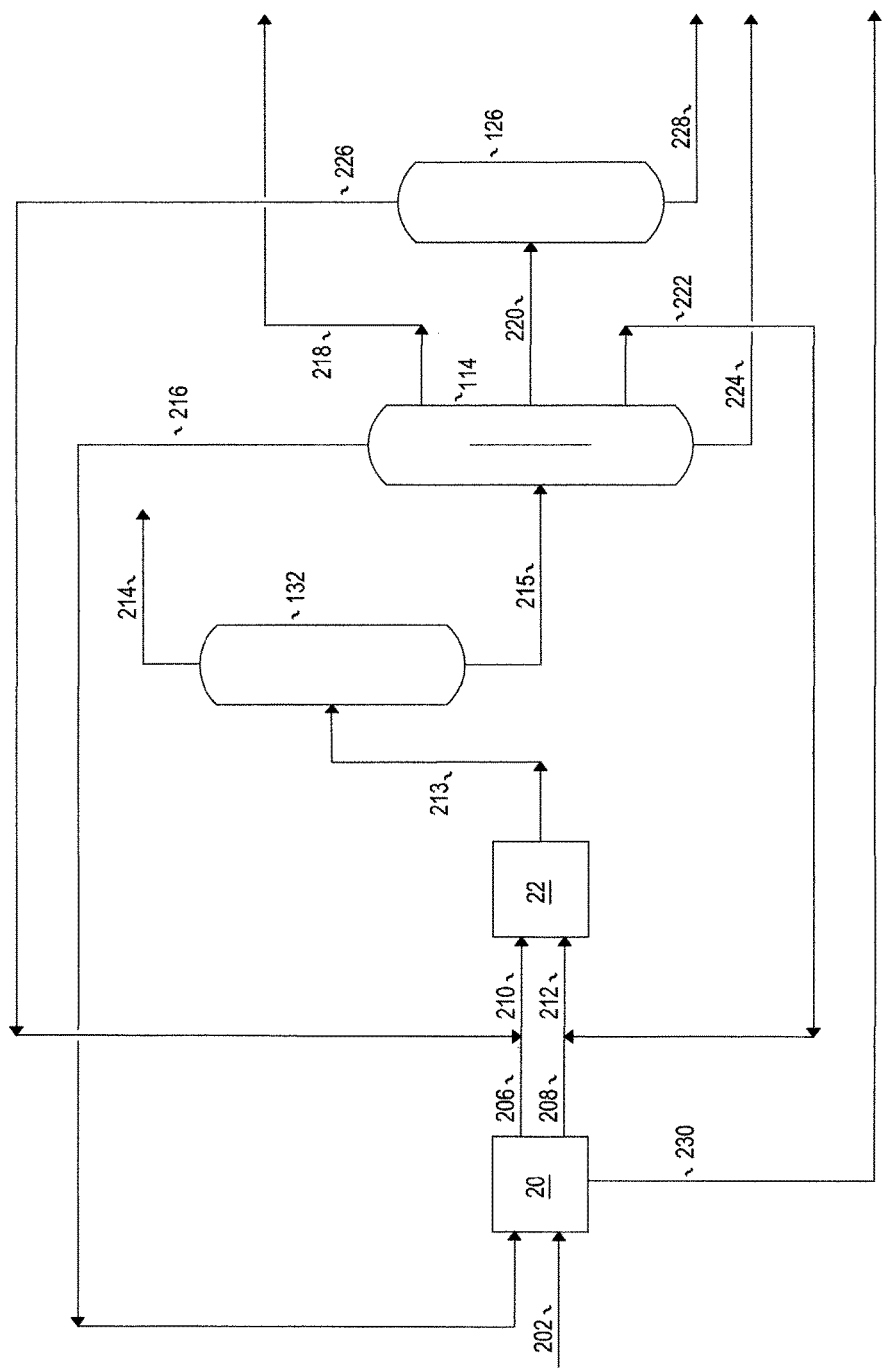
FIG. 3 provides a simplified process flow diagram of a second preferred embodiment of the invention.

A simplified process flow diagram of a second exemplary embodiment is shown in FIG. 3. The charge to the isomerization process is sent via line 202 to charge fractionation zone 20. Also shown entering the charge fractionation zone is a recycle stream from the isomerized product fractionation zone. The charge fractionation zone may produce one or more primary feeds to the isomerization zone. An isopentane stream is also removed from the charge fractionation zone via line 230 as a high octane isomerate product stream. Two primary feeds to the isomerization zone are shown in FIG. 3. The two primary feeds are conducted from the charge fractionation zone to the isomerization zone via lines 206 and 208. In this exemplary embodiment of the invention, the stream that is conducted via line 206 represents a C5-C6 fraction and the stream that is conducted via line 208 represents a C7 fraction. Two recycle streams from the isomerized product fractionation zone are also sent to the isomerization zone. A C6 rich recycle stream is conducted via line 226 and mixed with the C5-C6 fraction primary feed to create a combined C5-C6 isomerization zone feed stream which is conducted via line 210 to the isomerization zone. A C7 rich recycle stream is conducted via line 222 and mixed with the C7 fraction primary feed to create a combined C7 isomerization zone feed stream which is conducted via line 212 to the isomerization zone.

Isomerization zone 22 shown in FIG. 3 illustrates the isomerization equipment and processes used to efficiently isomerize the isomerization zone feeds which are conducted via lines 210 and 212 to the isomerization zone. Each of the isomerization zone feeds are isomerized in isomerization zone 22 in the presence of isomerization catalysts and hydrogen. Isomerization may take place in one or more isomerization reactor systems, wherein a reactor system may contain one or more isomerization reactors in series arrangement. Each isomerization reactor system may contain different isomerization catalysts and each reactor system may operate at different isomerization conditions in order to efficiently isomerize the isomerization zone feeds. In the exemplary embodiment of the invention shown in FIG. 3, the C5-C6 isomerization zone feed is intended to be isomerized in an isomerization reactor system designed for isomerizing C5-C6 feeds and the C7 isomerization zone feed is intended to be isomerized in an isomerization reactor system designed for isomerizing C7 feeds. The reactor effluent streams from all of the reactor systems are combined into a single combined isomerization zone effluent in the exemplary embodiment shown in FIG. 3. In the present invention, however, more than one isomerization zone effluent may be sent from the isomerization zone to the isomerized product fractionation zone.

The combined isomerization reactor effluent stream from isomerization zone 22 is sent to stabilizer 132 via line 213 to remove butane and lighter hydrocarbons. A stabilized isomerized product is removed from the second end of stabilizer 132 and sent to a fractionation system consisting of a dividing wall column and a non-divided column to separate high octane streams from low octane streams. Butane and lighter hydrocarbons are removed from the first end of stabilizer 132 via line 214. The stabilized isomerized product is sent to dividing wall column 114 via line 215.

The stabilized isomerized product is introduced at an intermediate point to the feed side, or first parallel fractionation zone, of the dividing wall column. The entirety of Fraction A as well as a portion of Fractions B and C are driven upwards in the first parallel fractionation zone and enter the upper undivided section of the column. In the upper undivided section of the column, Fraction A is separated into two subfractions and the portions of Fractions B and C which were driven upwards in the first parallel fractionation zone drain down into the second parallel fractionation zone. Fraction A is separated in the upper undivided section of the column into a C5 subfraction which is removed via line 216 from the first end of the column and returned to the charge fractionation zone and a C6 subfraction which is removed via line 218 as a first side draw from the column. The C6 subfraction is removed from the process as a high octane isomerate product stream.

The entirety of Fractions D and E as well as a portion of Fractions B and C drain down through the first parallel fractionation zone and enter the lower undivided section of the column. The portions of Fractions B and C which drained down through the first parallel fractionation zone are driven upward into the second parallel fractionation zone. Within the second parallel fractionation zone, the portions of Fractions B and C which were driven upwards in the first parallel fractionation zone and drained down into the second parallel fractionation zone combine with the portions of Fractions B and C which drained down through the first parallel fractionation zone and were driven upward into the second parallel fractionation zone. The entirety of Fractions B and C are removed from an intermediate point in the second parallel fractionation zone via line 220 as a second side draw from the column.

In the lower undivided section of the column, Fraction E drains down to the bottom of the column and Fraction D drains down to an intermediate point in the lower undivided section of the column. Fraction E is removed via line 224 from the second end of the column as a high octane isomerate product stream. Fraction D is removed via line 222 from an intermediate point in the lower undivided section of the column as a third side draw from the column and returned to the isomerization zone.

The mixture containing Fractions B and C that is removed from an intermediate point of the second parallel fractionation zone of the column is sent to an intermediate point in non-divided column 126, where Fraction B is separated from Fraction C. Fraction B is removed from the first end of the column and returned via line 226 to the isomerization zone. Fraction C is removed from the second end of the column via line 228 as a high octane isomerate product stream.

The composite high octane isomerate product from the overall isomerization process in the second exemplary embodiment is comprised from the sum of Fraction C, Fraction E and a portion of Fraction A. In this embodiment of the invention, Fraction A is divided into two subfractions. The first subfraction, a C5 subfraction, is sent from the first end of the dividing wall column via line 216 to charge fractionation zone 20, where it is separated into a high octane isopentane stream that is removed from the charge fractionation zone via line 230 and a low octane normal pentane stream, which is sent via line 206 to isomerization zone 22 together with the primary C5-C6 feed. The second subfraction, a C6 subfraction, is removed via line 218 as a first side draw from dividing wall column 114 in the isomerized product fractionation zone. The portion of Fraction A that is included in the composite high octane isomerate product from the overall isomerization process consists of the isopentane stream that is removed from the charge fractionation zone via line 230 plus the C6 subfraction that is removed from the dividing wall column via line 218 in the isomerized product fractionation zone.

In the second exemplary embodiment of the invention shown in FIG. 3, five streams are removed from the dividing wall column. In this embodiment, Fractions D and E are separated in the lower undivided section of the dividing wall column. It is also possible, however, to perform the separation of Fractions D and E in a second non-divided column by removing only four streams rather than five from the dividing wall column. In a scenario where Fractions D and E are separated in a second non-divided column, the entirety of Fractions D and E drain down to the bottom of the dividing wall column. The stream removed from the second end of the dividing wall column containing a mixture of Fractions D and E would be sent to a second non-divided column to separate Fractions D and E.

A third embodiment of the invention may be used in certain applications in which the designer prefers to keep the isomerized product streams segregated rather than combining these streams in the isomerization zone. The isomerized product streams may be intentionally segregated, for example, to reduce the fractionation energy input to the dividing wall column in the isomerized product fractionation zone. It may be possible to reduce the fractionation energy input by introducing the C7 rich stabilized isomerized product stream and the C5-C6 rich stabilized isomerized product stream to different feed tray locations in the dividing wall column versus a design in which the C7 rich stream and the C5-C6 rich stream are combined and introduced to the dividing wall column at a single feed tray location.

Figure 4:
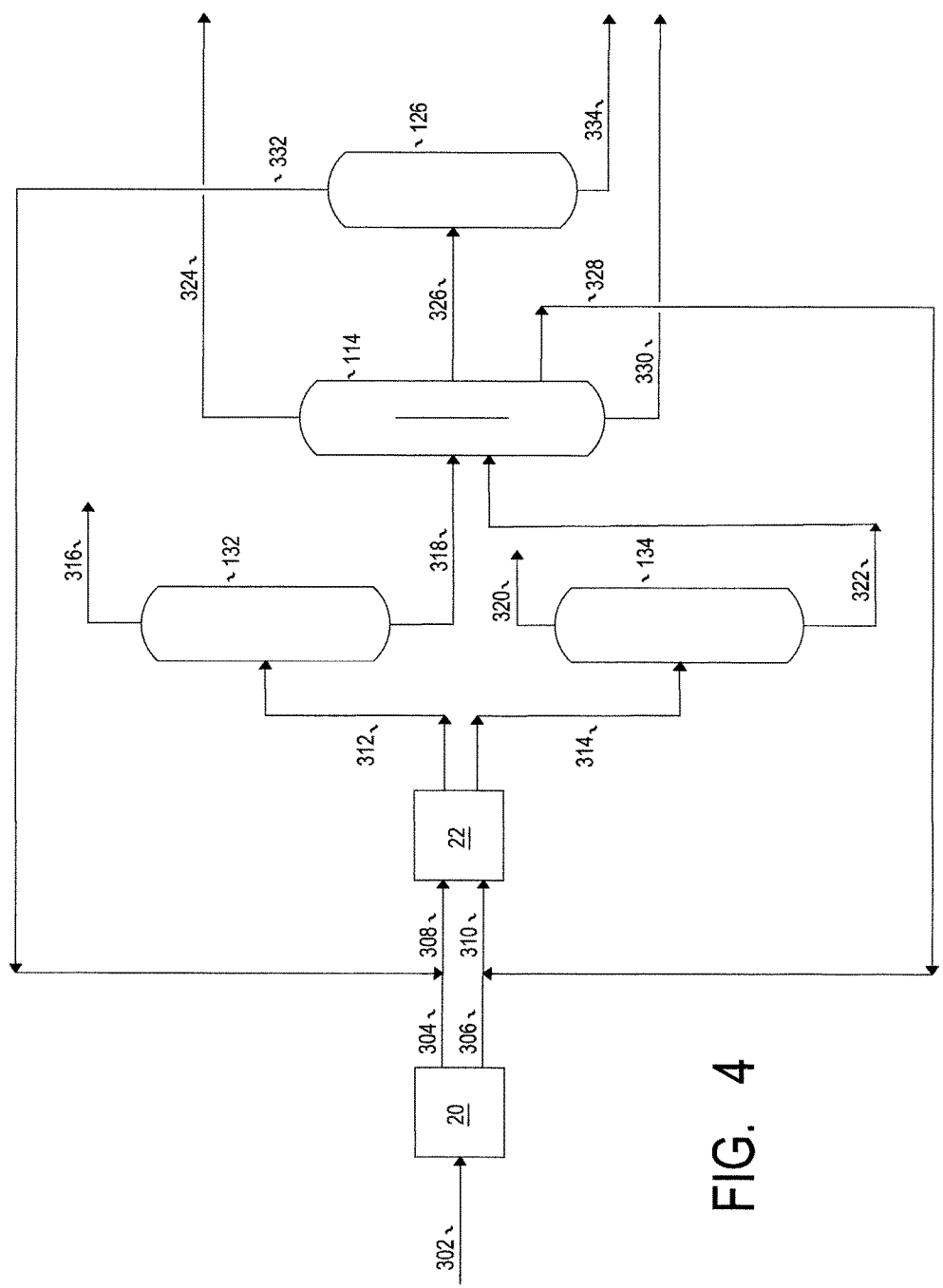
FIG. 4 provides a simplified process flow diagram of a third preferred embodiment of the invention.

A simplified process flow diagram of a third exemplary embodiment is shown in FIG. 4. The charge to the isomerization process is sent via line 302 to charge fractionation zone 20. The charge fractionation zone may produce one or more primary feeds to the isomerization zone. Two primary feeds to the isomerization zone are shown in FIG. 4. The two primary feeds are conducted from the charge fractionation zone 20 to isomerization zone 22 via lines 304 and 306. In this exemplary embodiment of the invention, the stream that is conducted via line 304 represents a C5-C6 fraction and the stream that is conducted via line 306 represents a C7 fraction. Two recycle streams from the isomerized product fractionation zone are also sent to the isomerization zone. A C6 rich recycle stream is conducted via line 332 and mixed with the C5-C6 fraction primary feed to create a combined C5-C6 isomerization zone feed stream which is conducted via line 308 to isomerization zone 22. A C7 rich recycle stream is conducted via line 328 and mixed with the C7 fraction primary feed to create a combined C7 isomerization zone feed stream which is conducted via line 310 to isomerization zone 22.

Isomerization zone 22 shown In FIG. 4 illustrates the isomerization equipment and processes used to efficiently isomerize the isomerization zone feeds which are conducted via lines 308 and 310 to the isomerization zone. Each of the isomerization zone feeds are isomerized in isomerization zone 22 in the presence of isomerization catalysts and hydrogen. Isomerization may take place in one or more isomerization reactor systems, wherein a reactor system may contain one or more isomerization reactors in series arrangement. Each isomerization reactor system may contain different isomerization catalysts and each reactor system may operate at different isomerization conditions in order to efficiently isomerize the isomerization zone feeds. In the exemplary embodiment of the invention shown in FIG. 4, the C5-C6 isomerization zone feed is intended to be isomerized in an isomerization reactor system designed for isomerizing C5-C6 feeds and the C7 isomerization zone feed is intended to be isomerized in an isomerization reactor system designed for isomerizing C7 feeds.

Each of the effluent streams from the isomerization reactors which are removed from isomerization zone 22 are sent to a stabilizer to remove butane and lighter hydrocarbons. The effluent stream from the isomerization reactor system which isomerizes the C5-C6 reactor feed fraction is removed from isomerization zone 22 and sent to stabilizer 132 via line 312 and the effluent stream from the isomerization reactor system which isomerizes the C7 reactor feed fraction is removed from isomerization zone 22 and sent to stabilizer 134 via line 314. A stabilized isomerized product is removed from the second end of each stabilizer and sent to a fractionation system consisting of a dividing wall column and a non-divided column to separate high octane streams from low octane streams. Butane and lighter hydrocarbons are removed from the first end of stabilizer 132 via line 316 and from the first end of stabilizer 134 via line 320. The stabilized isomerized product from stabilizer 132 is sent to dividing wall column 114 via line 318 and the stabilized isomerized product from stabilizer 134 is sent to dividing wall column 114 via line 322.

The stabilized isomerized product from stabilizer 132 is introduced at an intermediate point to the feed side, or first parallel fractionation zone, of the dividing wall column. The stabilized isomerized product from stabilizer 134 may be introduced at an intermediate point to the feed side, or first parallel fractionation zone, of the dividing wall column, or alternatively may be introduced to an intermediate point in the undivided section of the dividing wall column which is below the first and second parallel fraction zones. The selection of the location where the stabilized isomerized product from stabilizer 134 is introduced to the dividing wall column will depend on the concentration of multibranched C5 and C6 molecules in the stabilized isomerized product from stabilizer 134; if the concentration of multibranched C5 and C6 molecules in the stabilized isomerized product from stabilizer 134 is very low, it may be advantageous to introduce the stabilized isomerized product from stabilizer 134 at an intermediate point in the undivided section of the dividing wall column which is below the first and second parallel fraction zones. The entirety of Fraction A as well as a portion of Fractions B and C are driven upwards in the first parallel fractionation zone and enter the upper undivided section of the column. In the upper undivided section of the column, Fraction A is driven upwards to the top of the column and the portions of Fractions B and C which were driven upwards in the first parallel fractionation zone drain down into the second parallel fractionation zone. Fraction A is removed via line 324 from the first end of the column as a high octane isomerate product stream.

The entirety of Fractions D and E as well as a portion of Fractions B and C drain down through the first parallel fractionation zone and enter the lower undivided section of the column. The portions of Fractions B and C which drained down through the first parallel fractionation zone are driven upward into the second parallel fractionation zone.

Within the second parallel fractionation zone, the portions of Fractions B and C which were driven upwards in the first parallel fractionation zone and drained down into the second parallel fractionation zone combine with the portions of Fractions B and C which drained down through the first parallel fractionation zone and were driven upward into the second parallel fractionation zone. The entirety of Fractions B and C are removed from an intermediate point in the second parallel fractionation zone via line 326 as a first side draw from the column.

In the lower undivided section of the column, Fraction E drains down to the bottom of the column and Fraction D drains down to an intermediate point in the lower undivided section of the column. Fraction E is removed via line 330 from the second end of the column as a high octane isomerate product stream. Fraction D is removed via line 328 from an intermediate point in the lower undivided section of the column as a second side draw from the column and returned to the isomerization zone.

The mixture containing Fractions B and C that is removed from an intermediate point of the second parallel fractionation zone of the column is sent via line 326 to an intermediate point in non-divided column 126, where Fraction B is separated from Fraction C. Fraction B is removed from the first end of the column and returned via line 332 to the isomerization zone. Fraction C is removed from the second end of the column via line 334 as a high octane isomerate product stream.

The composite high octane isomerate product from the overall isomerization process in the first exemplary embodiment is comprised from the sum of Fractions A, C, and E. Each of these three fractions are removed from the isomerized product fractionation zone and combined to form the composite isomerate product from the overall isomerization process.

In the third exemplary embodiment of the invention shown in FIG. 4, four streams are removed from the dividing wall column. In this embodiment, Fractions D and E are separated in the lower undivided section of the dividing wall column. It is also possible, however, to perform the separation of Fractions D and E in a second non-divided column by removing only three streams rather than four from the dividing wall column. In the scenario where Fractions D and E are separated in a second non-divided column, the entirety of Fractions D and E drain down to the bottom of the dividing wall column. The stream removed from the second end of the dividing wall column containing a mixture of Fractions D and E would be sent to a second non-divided column to separate Fractions D and E.

A fourth embodiment of the invention may be used in certain applications which do not require a sharp separation between Fraction B (containing the major portion of normal hexane and paraffins containing 6 carbon atoms with a single branch) and Fraction C (containing the major portion of paraffins containing 7 carbon atoms with at least two branches), such as some applications with less stringent composite isomerate product RON targets. In these applications, it may be possible to perform the separation of the stabilized isomerized product stream using only a dividing wall column. The advantage afforded by performing the separation of the stabilized isomerized product stream using only a dividing wall column is that capital costs for the isomerization unit are reduced by eliminating the need for a non-divided column to perform the separation between Fractions B and C.

Figure 5:
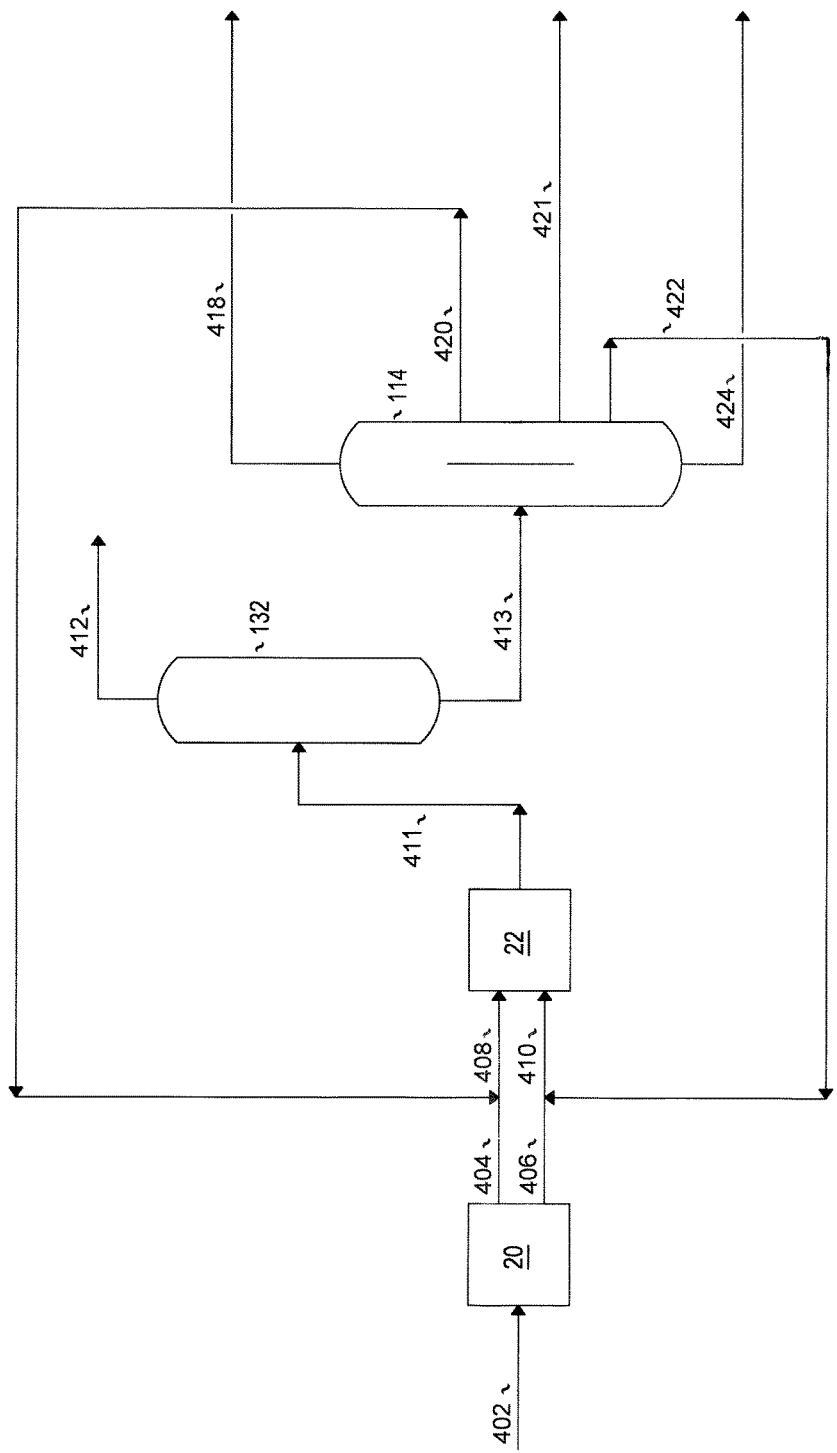
FIG. 5 provides a simplified process flow diagram of a fourth preferred embodiment of the invention.

A fourth exemplary embodiment of the invention is shown in FIG. 5. The charge to the isomerization process is sent via line 402 to charge fractionation zone 20. The charge fractionation zone may produce one or more primary feeds to the isomerization zone. Two primary feeds to the isomerization zone are shown in FIG. 5. The two primary feeds are conducted from the charge fractionation zone 20 to isomerization zone 22 via lines 404 and 406. In this exemplary embodiment of the invention, the stream that is conducted via line 404 represents a C5-C6 fraction and the stream that is conducted via line 406 represents a C7 fraction. Two recycle streams from the isomerized product fractionation zone are also sent to the isomerization zone. A C6 rich recycle stream is conducted via line 420 and mixed with the C5-C6 fraction primary feed to create a combined C5-C6 isomerization zone feed stream which is conducted via line 408 to isomerization zone 22. A C7 rich recycle stream is conducted via line 422 and mixed with the C7 fraction primary feed to create a combined C7 isomerization zone feed stream which is conducted via line 410 to isomerization zone 22.

Isomerization zone 22 shown In FIG. 5 illustrates the isomerization equipment and processes used to efficiently isomerize the isomerization zone feeds which are conducted via lines 408 and 410 to the isomerization zone. Each of the isomerization zone feeds are isomerized in isomerization zone 22 in the presence of isomerization catalysts and hydrogen. Isomerization may take place in one or more isomerization reactor systems, wherein a reactor system may contain one or more isomerization reactors in series arrangement. Each isomerization reactor system may contain different isomerization catalysts and each reactor system may operate at different isomerization conditions in order to efficiently isomerize the isomerization zone feeds. In the exemplary embodiment of the invention shown in FIG. 5, the C5-C6 isomerization zone feed is intended to be isomerized in an isomerization reactor system designed for isomerizing C5-C6 feeds and the C7 isomerization zone feed is intended to be isomerized in an isomerization reactor system designed for isomerizing C7 feeds. The reactor effluent streams from all of the reactor systems are combined into a single combined isomerization zone effluent in the exemplary embodiment shown in FIG. 5. In the present invention, however, more than one isomerization zone effluent may be sent from the isomerization zone to the isomerized product fractionation zone.

The combined effluent stream from the isomerization reactors which is removed from isomerization zone 22 is sent to stabilizer 132 via line 411 to remove butane and light gases. A stabilized isomerized product is removed from the second end of stabilizer 132 and sent to a dividing wall column to separate high octane streams from low octane streams. Butane and light gases are removed from the first end of stabilizer 132 via line 412. The stabilized isomerized product is sent to dividing wall column 114 via line 413.

The stabilized isomerized product is introduced at an intermediate point to the feed side, or first parallel fractionation zone, of the dividing wall column. The entirety of Fraction A as well as a portion of Fractions B and C are driven upwards in the first parallel fractionation zone and enter the upper undivided section of the column. In the upper undivided section of the column, Fraction A is driven upwards to the top of the column and the portions of Fractions B and C which were driven upwards in the first parallel fractionation zone drain down into the second parallel fractionation zone. Fraction A is removed via line 418 from the first end of the column as a high octane isomerate product stream.

The entirety of Fractions D and E as well as a portion of Fractions B and C drain down through the first parallel fractionation zone and enter the lower undivided section of the column. The portions of Fractions B and C which drained down through the first parallel fractionation zone are driven upward into the second parallel fractionation zone.

A separation between Fraction B and Fraction C takes place in the second parallel fractionation zone. The portions of Fractions B and C which were driven upwards in the first parallel fractionation zone drain down into the top of the second parallel fractionation zone and the portions of Fractions B and C which drained down through the first parallel fractionation zone are driven upward into the bottom of the second parallel fractionation zone. Since Fraction B boils at a lower temperature than Fraction C, Fraction B will concentrate in the upper part of the second parallel fractionation zone and Fraction C will concentrate in the lower part of the second parallel fractionation zone. Fraction B is removed from the second parallel fractionation zone via line 420 as a first side draw from the column and returned to the isomerization zone. Fraction C is removed from the second parallel fractionation zone via line 421 as a second side draw from the column as a high octane isomerate product stream. Fraction B is removed from the column at an elevation that is higher than the elevation at which Fraction C is removed from the column.

In the lower undivided section of the column, Fraction E drains down to the bottom of the column and Fraction D drains down to an intermediate point in the lower undivided section of the column. Fraction E is removed via line 424 from the second end of the column as a high octane isomerate product stream. Fraction D is removed via line 422 from an intermediate point in the lower undivided section of the column as a third side draw from the column and returned to the isomerization zone.

The composite high octane isomerate product from the overall isomerization process in the first exemplary embodiment is comprised from the sum of Fractions A, C, and E. Each of these three fractions are removed from the isomerized product fractionation zone and combined to form the composite isomerate product from the overall isomerization process.

In the fourth exemplary embodiment of the invention shown in FIG. 5, five streams are removed from the dividing wall column. In this embodiment, Fractions D and E are separated in the lower undivided section of the dividing wall column. It is also possible, however, to perform the separation of Fractions D and E in a non-divided column by removing only four streams rather than five from the dividing wall column. In a scenario where Fractions D and E are separated in a non-divided column, the entirety of Fractions D and E drain down to the bottom of the dividing wall column. The stream removed from the second end of the dividing wall column containing a mixture of Fractions D and E would be sent to a non-divided column to separate Fractions D and E.

The invention claimed is:
1. An isomerization process having an isomerized product fractionation zone, said process comprising:
   contacting one or more feeds comprising at least one component selected from the group consisting of normal pentane, normal hexane, and normal heptane with an isomerization catalyst in one or more isomerization reactors in an isomerization zone to convert at least a portion of the at least one component to isomerized products and form one or more isomerization reactor effluent streams which are combined into a single isomerization zone effluent,
   wherein the isomerization zone effluent comprises $C_5$-$C_7$ normal and branched paraffins,
   and wherein each isomerization reactor may contain different isomerization catalysts and each reactor may operate at different isomerization conditions;
   passing the isomerization zone effluent into a stabilizer to remove butane and light gases and form a stabilized isomerized product;
   passing the stabilized isomerized product into a dividing wall column divided into at least a first and second parallel fractionation zones by a dividing wall, with the first and second fractionation zones each having an upper end and a lower end located within the dividing wall column, wherein the first and second parallel fractionation zones are in open communication at the upper ends with an undivided upper section of the column and wherein the first and second parallel fractionation zones are in open communication at the lower ends with an undivided lower section of the column, and wherein the stabilized isomerized product enters the column at an intermediate point in the first parallel fractionation zone; and
   removing at least three streams from the dividing wall column, wherein
   i) a single side stream comprising normal hexane, paraffins containing 6 carbon atoms and a single branch, and paraffins containing 7 carbon atoms with at least two branches is removed from an intermediate point of the second parallel fractionation zone of the dividing wall column, or
   ii) a low octane stream comprising normal hexane and paraffins containing 6 carbon atoms and a single branch is removed as a first side stream from the second parallel fractionation zone of the dividing wall column, and a high octane stream comprising paraffins containing 7 carbon atoms with at least two branches is removed as a second side stream from the second parallel fractionation zone of the dividing wall column.

2. The process according to claim 1, wherein said single side stream comprising normal hexane, paraffins containing 6 carbon atoms and a single branch, and paraffins containing 7 carbon atoms with at least two branches is removed from an intermediate point of the second parallel fractionation zone of the dividing wall column and passed to a non-divided column.

3. The process according to claim 2, wherein a low octane stream comprising normal hexane and paraffins containing 6 carbon atoms and a single branch is removed from a first end of the non-divided column; and wherein a high octane stream comprising paraffins containing 7 carbon atoms with at least two branches is removed from a second end of the non-divided column.

4. The process according to claim 1, wherein a high octane stream comprising hydrocarbon containing 5 carbon atoms and paraffins containing 6 carbon atoms with at least two branches is removed from a first end of the dividing wall column.

5. The process according to claim 1, wherein a high octane stream comprising hydrocarbons containing at least 8 carbon atoms is removed from a second end of the dividing wall column.

6. The process according to claim 1, wherein a low octane stream comprising normal heptane and paraffins containing 7 carbon atoms and a single branch is removed as a side stream from an intermediate point in the undivided lower section of the dividing wall column.

7. The process according to claim 1, wherein an intermediate stream comprising hydrocarbon containing 5 carbon atoms is removed from a first end of the dividing wall column and passed to a feed fractionation zone, wherein a majority of isopentane molecules are removed from said intermediate stream and recovered as a high octane stream in the feed fractionation zone.

8. The process according to claim 7, wherein a high octane stream comprising paraffins containing 6 carbon atoms with at least two branches is removed as a side stream from an intermediate point in the undivided upper section of the dividing wall column.

9. An isomerization process having an isomerized product fractionation zone, said process comprising:
   contacting one or more feeds comprising at least one component selected from the group consisting of normal pentane, normal hexane, and normal heptane with an isomerization catalyst in one or more isomerization reactors in an isomerization zone to convert at least a portion of the at least one component to isomerized products and form one or more isomerization reactor effluent streams;
   passing each of said isomerization reactor effluent streams into one or more stabilizers to remove butane and light gases and form one or more stabilized isomerized product streams, wherein each of the isomerization reactor effluent streams is passed into separate stabilizers without combining isomerization reactor effluent streams;
   passing each of the said stabilized isomerized product streams into a common dividing wall column divided into at least a first and second parallel fractionation zones by a dividing wall, with the first and second fractionation zones each having an upper end and a lower end located within the dividing wall column, wherein the first and second parallel fractionation zones are in open communication at the upper ends with an undivided upper section of the column and wherein the first and second parallel fractionation zones are in open communication at the lower ends with an undivided lower section of the column, and wherein each of the stabilized isomerized product streams enters the column at an intermediate point in the first parallel fractionation zone or alternatively enters the column at an intermediate point in the undivided lower section of the column; and
   removing at least three streams from the dividing wall column, wherein
   i) a single side stream comprising normal hexane, paraffins containing 6 carbon atoms and a single branch, and paraffins containing 7 carbon atoms with at least two branches is removed from an intermediate point of the second parallel fractionation zone of the dividing wall column, or ii) a low octane stream comprising normal hexane and paraffins containing 6 carbon atoms and a single branch is removed as a first side stream from the second parallel fractionation zone of the dividing wall column, and a high octane stream comprising paraffins containing 7 carbon atoms with at least two branches is removed as a second side stream from the second parallel fractionation zone of the dividing wall column.

10. The process according to claim 9, wherein a said single side stream comprising normal hexane, paraffins containing 6 carbon atoms and a single branch, and paraffins containing 7 carbon atoms with at least two branches is removed from an intermediate point of the second parallel fractionation zone of the dividing wall column and passed to a non-divided column.

11. The process according to claim 10, wherein a low octane stream comprising normal hexane and paraffins containing 6 carbon atoms and a single branch is removed from a first end of the non-divided column; and wherein a high octane stream comprising paraffins containing 7 carbon atoms with at least two branches is removed from a second end of the non-divided column.

12. The process according to claim 9, wherein a high octane stream comprising hydrocarbons containing 5 carbon atoms and paraffins containing 6 carbon atoms with at least two branches is removed from a first end of the dividing wall column.

13. The process according to claim 9, wherein a high octane stream comprising hydrocarbons containing at least 8 carbon atoms is removed from a second end of the dividing wall column.

14. The process according to claim 1, wherein a low octane stream comprising normal heptane and paraffins containing 7 carbon atoms and a single branch is removed as a side stream from an intermediate point in the undivided lower section of the dividing wall column.

15. The process according to claim 9, wherein an intermediate stream comprising hydrocarbon containing 5 carbon atoms is removed from a first end of the dividing wall column and passed to a feed fractionation zone, wherein a majority of isopentane molecules are removed from said intermediate stream and recovered as a high octane stream in the feed fractionation zone.

16. The process according to claim 15, wherein a high octane stream comprising paraffins containing 6 carbon atoms with at least two branches is removed as a side stream from an intermediate point in the undivided upper section of the dividing wall column.

17. A process for separating an isomerization zone effluent in a product fractionation zone comprising a stabilizer and a dividing wall column, comprising:

passing an isomerization zone effluent comprising C5-C7 normal and branched paraffins to a stabilizer to remove butane and light gases and form a stabilized isomerized product;

passing the stabilized isomerized product into a dividing wall column divided into at least a first and second parallel fractionation zones by a dividing wall, with the first and second fractionation zones each having an upper end and a lower end located within the dividing wall column, wherein the first and second parallel fractionation zones are in open communication at the upper ends with an undivided upper section of the column and wherein the first and second parallel fractionation zones are in open communication at the lower ends with an undivided lower section of the column, and wherein the stabilized isomerized product enters the column at an intermediate point in the first parallel fractionation zone; and removing at least three streams from the dividing wall column, wherein i) a single side stream comprising normal hexane, paraffins containing 6 carbon atoms and a single branch, and paraffins containing 7 carbon atoms with at least two branches is removed from an intermediate point of the second parallel fractionation zone of the dividing wall column, or ii) a low octane stream comprising normal hexane and paraffins containing 6 carbon atoms and a single branch is removed as a first side stream from the second parallel fractionation zone of the dividing wall column, and a high octane stream comprising paraffins containing 7 carbon atoms with at least two branches is removed as a second side stream from the second parallel fractionation zone of the dividing wall column.

* * * * *